(12) United States Patent
Al-Moosawi et al.

(10) Patent No.: US 7,705,291 B2
(45) Date of Patent: Apr. 27, 2010

(54) APPARATUS AND METHOD FOR WOUND DIAGNOSIS

(75) Inventors: Osama Al-Moosawi, Bear, DE (US); Sean M. Geary, Chadds Ford, PA (US)

(73) Assignee: Woundmatrix, Inc., Chadds Ford, PA (US)

( * ) Notice: Subject to any disclaimer, the term of this patent is extended or adjusted under 35 U.S.C. 154(b) by 0 days.

(21) Appl. No.: 12/263,380

(22) Filed: Oct. 31, 2008

(65) Prior Publication Data

US 2009/0116712 A1    May 7, 2009

Related U.S. Application Data

(60) Provisional application No. 60/985,100, filed on Nov. 2, 2007.

(51) Int. Cl.
*A61B 5/00*    (2006.01)
*G01V 8/00*    (2006.01)

(52) U.S. Cl. .................. 250/234; 250/559.21; 356/607; 382/128

(58) Field of Classification Search ................. 250/234, 250/235, 559.19, 559.21, 559.22; 356/606, 356/607, 626, 627; 382/128, 154
See application file for complete search history.

(56) References Cited

U.S. PATENT DOCUMENTS

| | | | |
|---|---|---|---|
| 4,070,683 A | | 1/1978 | Altschuler et al. |
| 4,294,544 A | | 10/1981 | Altschuler et al. |
| 4,483,075 A | * | 11/1984 | Kundin ......................... 331/21 |
| 4,535,782 A | * | 8/1985 | Zoltan ......................... 600/477 |
| 4,821,200 A | * | 4/1989 | Oberg ......................... 700/182 |
| 5,102,223 A | | 4/1992 | Uesugi et al. |
| 5,513,276 A | | 4/1996 | Theodoracatos |
| 5,619,587 A | | 4/1997 | Willoughby, Jr. et al. |

(Continued)

FOREIGN PATENT DOCUMENTS

| | | |
|---|---|---|
| JP | 2004-037396 A | 2/2004 |
| WO | 2005-033620 A2 | 4/2005 |
| WO | 2007-043899 A1 | 4/2007 |

OTHER PUBLICATIONS

Kundin, Jane I., "A New Way to Size Up a Wound", American Journal of Nursing, pp. 206-207, Feb. 1989.

(Continued)

*Primary Examiner*—John R Lee
(74) *Attorney, Agent, or Firm*—Sonnenschein Nath & Rosenthal (57) ABSTRACT

A configurable scanner (1), adapted for contactless measurement of the depth and perimeter of a wound on a target body part (9), has a scan head (4), and a processor (3) for controlling a scanning procedure and analyzing the results. The scan head is translated along a substantially semicircular path (7) having a configurable radial distance from an imaginary axis, such that the imaginary axis is approximately coincident with an axis of the target (9). The scan head (4) projects a contour line having a calibrated length onto the target surface, and the processor (3) stores an image of the projected contour line captured by an image capturing device (11). The processor (3) analyzes a series of captured images to determine the coordinates in three axes of the projected contour line, creates therefrom a 3D model of the region of interest, and determines a depth and perimeter of the wound from the 3D model.

2 Claims, 9 Drawing Sheets

U.S. PATENT DOCUMENTS

| | | | |
|---|---|---|---|
| 6,195,455 | B1 | 2/2001 | Mack et al. |
| 6,493,095 | B1 * | 12/2002 | Song et al. ................. 356/603 |
| 6,611,267 | B2 | 8/2003 | Migdal et al. |
| 6,847,462 | B1 | 1/2005 | Kacyra et al. |
| 7,065,242 | B2 | 6/2006 | Petrov et al. |
| 7,068,836 | B1 | 6/2006 | Rubbert et al. |
| 7,181,363 | B2 | 2/2007 | Ratti et al. |
| 7,495,208 | B2 * | 2/2009 | Czarnek et al. ............. 250/234 |
| 2002/0149585 | A1 | 10/2002 | Kacyra et al. |
| 2003/0001835 | A1 | 1/2003 | Dimsdale et al. |
| 2003/0105611 | A1 | 6/2003 | Sachdeva |
| 2003/0137510 | A1 | 7/2003 | Massen |
| 2004/0263862 | A1 | 12/2004 | Amparan et al. |
| 2005/0033142 | A1 | 2/2005 | Madden et al. |
| 2005/0099637 | A1 | 5/2005 | Kacyra et al. |
| 2006/0055943 | A1 | 3/2006 | Kawasaki et al. |
| 2007/0276195 | A1 * | 11/2007 | Xu et al. .................... 600/300 |
| 2007/0285650 | A1 * | 12/2007 | Kerner et al. ................. 356/30 |
| 2009/0116712 | A1 * | 5/2009 | Al-Moosawi et al. ....... 382/128 |

OTHER PUBLICATIONS

Langemo, Daiane K., "Comparison of 2 Wound Volume Measurement Methods", Adv. Skin Wound Care, vol. 14, pp. 190-196, Jul. 2001; found at http://findarticles.com/p/articles/mi_qa3977/is_200107/ai_n8998/print.

Pudner, Rosie, "Measuring Wounds", Journal of Community Nursing, vol. 16(09), pp. 36-42, Sep. 2002; found at http://www.jcn.co.uk/journal.asp?MonthNum=09&YearNum=2002&Type=backissue&A....

Quan, Susan Y. et al., "Digital Imaging of Wounds: Are Measurements Reproducible Among Observers?", Int. J. Lower Extremity Wounds, vol. 6(4), pp. 245-248, Dec. 2007; available at http://ijl.sagepub.com/cgi/content/abstract/6/4/245.

* cited by examiner

APPARATUS AND METHOD FOR WOUND DIAGNOSIS

CROSS REFERENCES TO RELATED APPLICATION

This patent application claims the benefit of U.S. provisional patent application 60/985,100 filed on Nov. 2, 2007, and entitled "Apparatus and Method for Wound Diagnosis", which provisional patent application is hereby incorporated by reference in its entirety into the present patent application.

TECHNICAL FIELD

The invention is related to wound diagnosis. More particularly, the invention provides for fast, accurate, and non-invasive measurement in three dimensions of the boundary, area, and volume of a wound.

BACKGROUND OF THE INVENTION

There is a long felt need in the medical community for improved methods of measuring the volume and perimeter of large wounds. As detailed in articles by Diane K. Langemer ("Comparison of 2 wound volume measurement methods," *Advances in Skin & Wound Care*, July/August 2001, hereinafter, "Langemer", hereby incorporated by reference into the present patent application in its entirety) and Rosie Pudner ("Measuring Wounds," *Journal of Community Nursing*, Volume 16, Issue 09, September 2002, hereinafter, "Pudner" hereby incorporated by reference into the present patent application in its entirety), known wound volume measurement techniques include wound molds, disposable gauges such as the Kundlin wound gauge (U.S. Pat. No. 4,483,075, hereby incorporated by reference into the present patent application in its entirety), and stereo photogrammetry (SPG).

Wound molds can provide relatively accurate measurement of wound volume but are time consuming, and expose a patient suffering from the wound to discomfort and risks of infection. The Kundlin gauge provides faster measurement capability relative to a wound mold, but still exposes the wound to contact with a foreign object (the gauge), thereby resulting in an increased risk of patient discomfort and infection. Moreover, accuracy and repeatability of the Kundlin gauge is relatively poor, and measurements using it still require 15-20 minutes. Langemer.

SPG is a non-invasive method that is reportedly more accurate then the Kundlin gauge, but the method is not suitable for certain types of wounds and is also time consuming and requires training. Pudner.

Use of structured light systems, e.g., laser scanners, for wound volume measurements has been considered. However, known techniques have proven ineffective for certain types of wounds, e.g., deep tracking wounds, large circumferential wounds, or wounds with undermining at the edges, and where the patient's position is not constant. Id. The problem of applying laser scanners to measurements of live subjects is discussed in Oberg, U.S. Pat. No. 4,821,200 (hereinafter, "Oberg") and Song, et al., U.S. Pat. No. 6,493,095 (hereinafter "Song"). Oberg describes a method of imaging and analyzing a laser line projected onto an amputee's stump. As illustrated in Oberg, FIG. 1, the method requires the subject to be immobilized in an apparatus during the measurement procedure. The apparatus described in Oberg is highly undesirable for use with a patient suffering from a large, unhealed wound. The practical problems of immobilizing a living being for the duration of a laser scanning procedure are also noted by Song, col. 1, ll. 43-44.

Fright, et al., PCT/NZ2006/000262, (hereinafter, "Fright") describes using optical triangulation with a camera and laser for wound volume estimation. The apparatus disclosed in Fright is stationary relative to the wound under inspection and is unable to accurately image nonplanar wounds. Since most large wounds have a substantial nonplanar aspect, this is a significant deficiency.

Thus, improved methods for non-invasive measurement in three dimensions of the boundary of a wound are needed.

DISCLOSURE OF INVENTION

In some embodiments of the present invention, a configurable scanner (1), adapted for contactless measurement of the depth and perimeter of a wound on a target body part (9), has a scan head (4) and a processor (3) for controlling a scanning procedure and analyzing the results. The configurable scanner (1) has a scanning module (2), scan head (4), positioning mechanism (6), and means for calibrating the scanning and positioning mechanisms.

DETAILED DESCRIPTION OF PREFERRED EMBODIMENTS

Figure 1A:
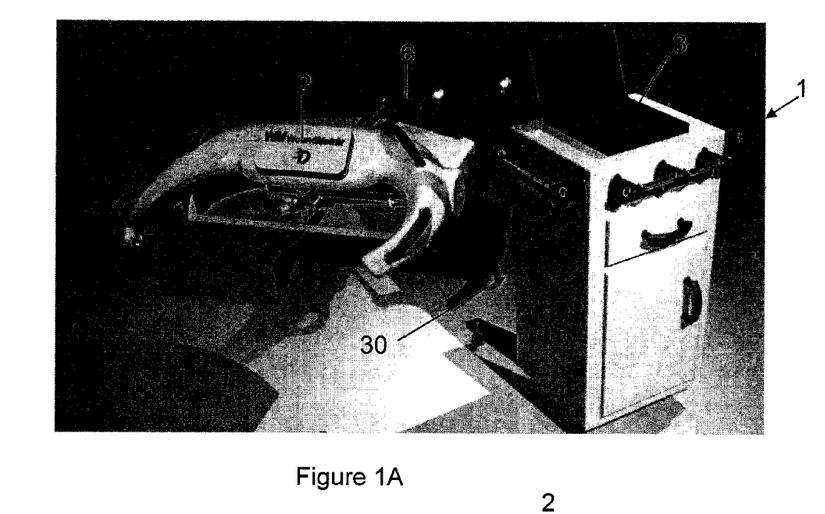
FIG. 1A illustrates a perspective view of a configurable scanner with a deployed scanning module.

Referring to FIG. 1A, configurable scanner 1 may include a work station 3, and a scanning module 2 coupled to the work station 3 by a positioning mechanism 6. The positioning mechanism 6 may consist of an articulable arm as illustrated in FIG. 1A, or by any other means. Advantageously, the positioning mechanism 6 provides six degrees of freedom to scanning module 2, and provides means for transference of electrical power as well as control signals and imaging data signals between the work station 30 and the scanning module 2. The work station 30 may include an operator interface and a processor 3 operable to control a scanning procedure and analyze the results. The processor 3 may be a personal computer, for example, and the operator interface may be provided via conventional keyboard, mouse and computer screen means, for example.

Figure 1B:
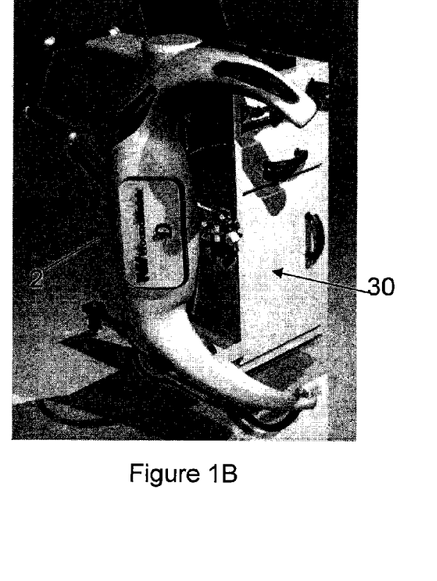
FIG. 1B illustrates a perspective view of the configurable scanner with a stowed scanning module.

The work station 30 may be embodied as a mobile cart, to which scanning module 2 and positioning mechanism 6 can be secured between scanning procedures, as shown in FIG. 1B. Thereby, configurable scanner 1 may be conveniently moved from patient to patient within a hospital or other clinical setting.

Figure 1C:
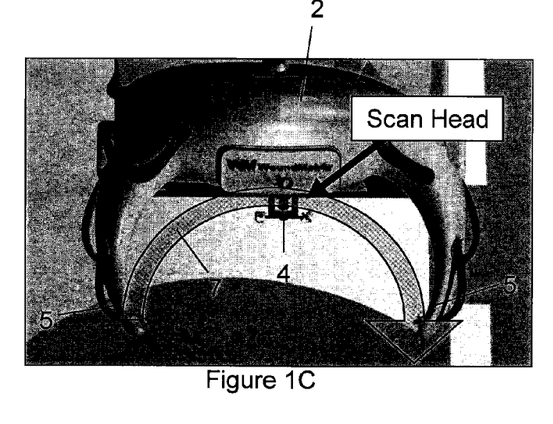
FIG. 1C illustrates a top view of the scanning module.

Referring now to FIG. 1C, scanning module 2 is illustrated in more detail. Scanning module 2 may include a scan head 4 that is translatable along a substantially semi-circular path 7. The radius of the semi-circular path 7 may be selectably adjustable. End points of path 7 are defined by arms 5 that extend from a main body of the scanning module; a point midway between arms 5 may define an axis of revolution of path 7. As will be described in more detail hereinafter, in preparation for and during a scanning procedure, arms 5 may be arranged to substantially envelope a target body part ("target object").

Figure 2A:
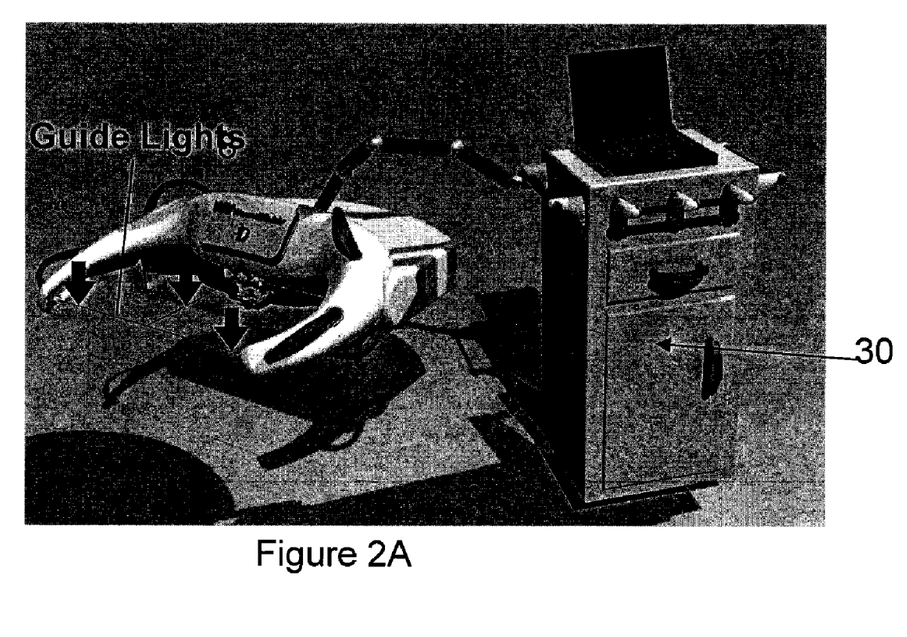
FIG. 2A presents a second perspective view of the configurable scanner in accordance, illustrating the use of guide lights.
Figure 2B:
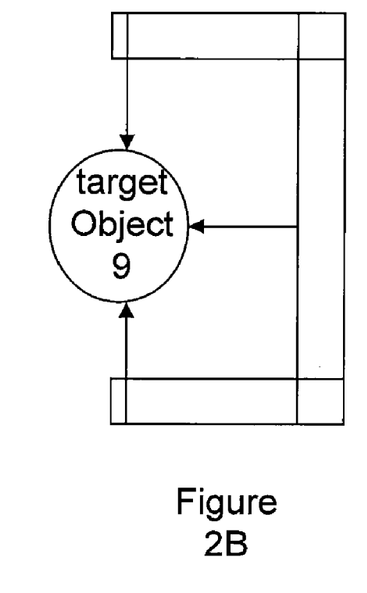
FIG. 2B is schematic top view illustrating the use of guide lights in conjunction with a target object.

Scanning module 2 is advantageously provided with guide lights 8 as illustrated in FIG. 2A where each guide light 8 is directed proximately toward the axis of revolution of path 7. Scanning module 2 may be operated after placing scanning module 2 such that an axis of the target object to be inspected, for example, an injured extremity or torso, coincides with the axis of revolution of path 7. Guide lights 8, which may, for example, be laser pointers, may be used as alignment aids to facilitate this positioning, as illustrated in FIG. 2B.

Figure 3A:
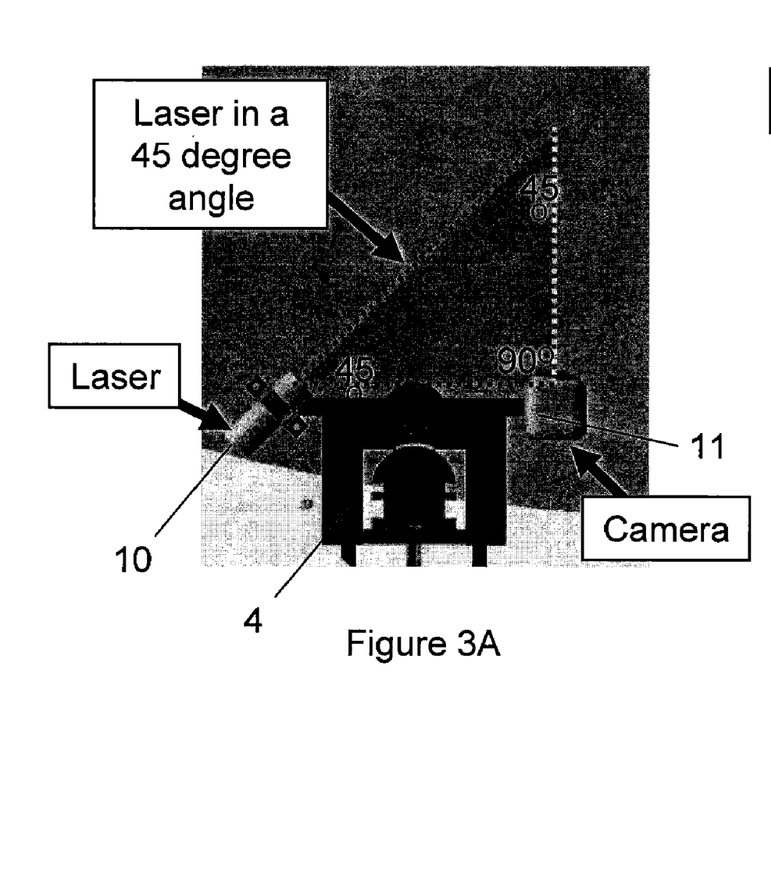
FIG. 3A illustrates a top view detail of a scan head.
Figure 4A:
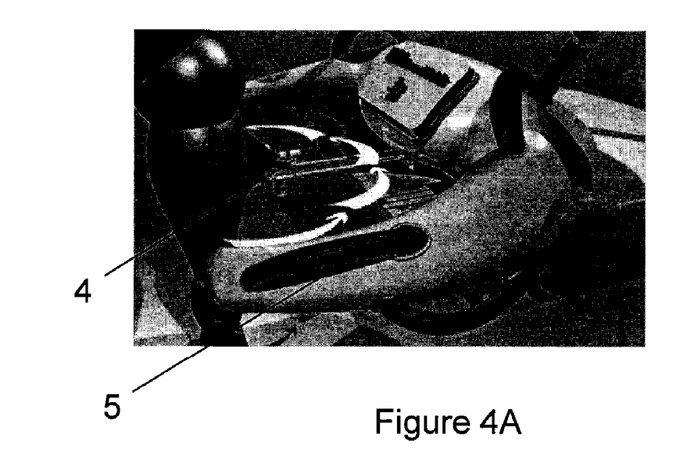
FIGS. 4A and 4B illustrate a perspective detail view of the scanning module in conjunction with a target object.
Figure 4B:
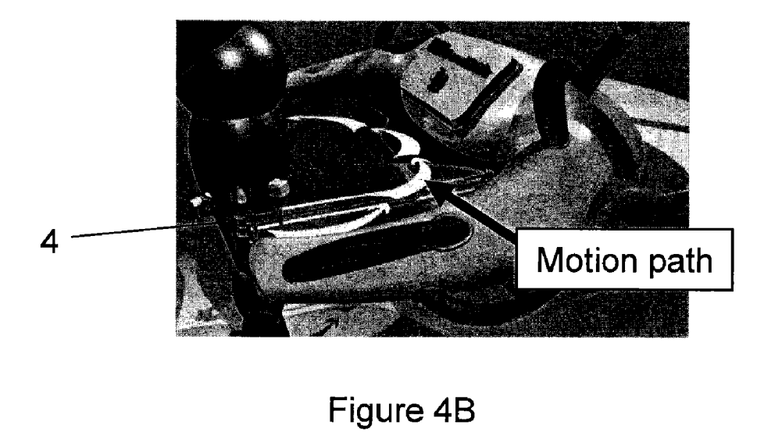

Referring to FIG. 3A, a detailed top view of scan head 4 is illustrated. Scan head 4 may include a light source 10 that can project a line of light, for example a line-laser, and an image capturing device 11. An illumination axis of laser 10 intercepts an optical axis of image capturing device 11 at a known angle. In an exemplary embodiment, the known angle may be 45 degrees. Scan head 4 may be operable to direct the optical axis of image capturing device 11 toward the axis of revolution of semi-circular path 7. Similarly, scan head 4 may be operable to direct the line projected by line laser 10 toward the axis of revolution of semi-circular path 7. Mechanical means may provide for simultaneous rotation and translation of scan head 4, so that the optical axis of image capturing device 11 and the line projected by line laser 10 both remain pointed toward the axis of revolution of semi-circular path 7 as the scan head 4 translates along semi-circular path 7. Exemplary means to provide this simultaneous rotation and translation are shown in FIG. 4.

Figure 3B:
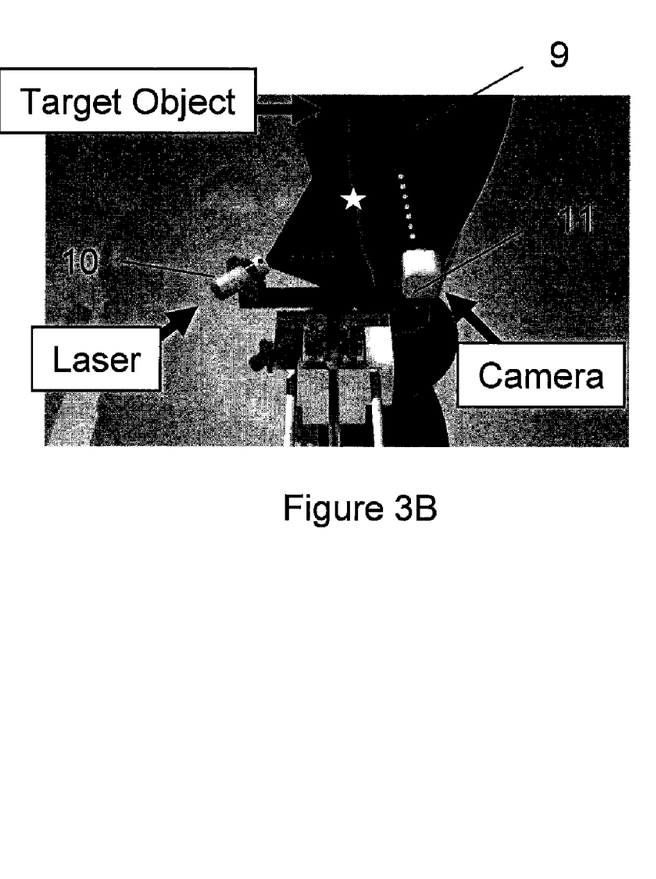
FIG. 3B illustrates operation of the scan head in conjunction with a target object.

Operation of the scan head 4 in conjunction with a target object of inspection 9 is illustrated in FIG. 3B. In a clinical setting, the target object 9 will be a body part, for example, a limb or torso of a patient. As noted above, prior to operation of the scan head, the module 2 is placed such that an axis of the target object 9, substantially coincides with the axis of revolution of path 7. Accordingly, the line projected by line-laser projector 10 and the optical axis of image capturing device 11 are each directed substantially toward the axis of target object 9. The line projected by line-laser projector 10, having a calibrated length, is projected onto the surface of target object 9, thereby forming projected illumination line 12. Image capturing device 11 has a field of view that includes illumination line 12. As viewed from image capturing device 11, the length and shape of illumination line 12, will vary as a function of the contour of the surface of target object 9.

Figure 5A:
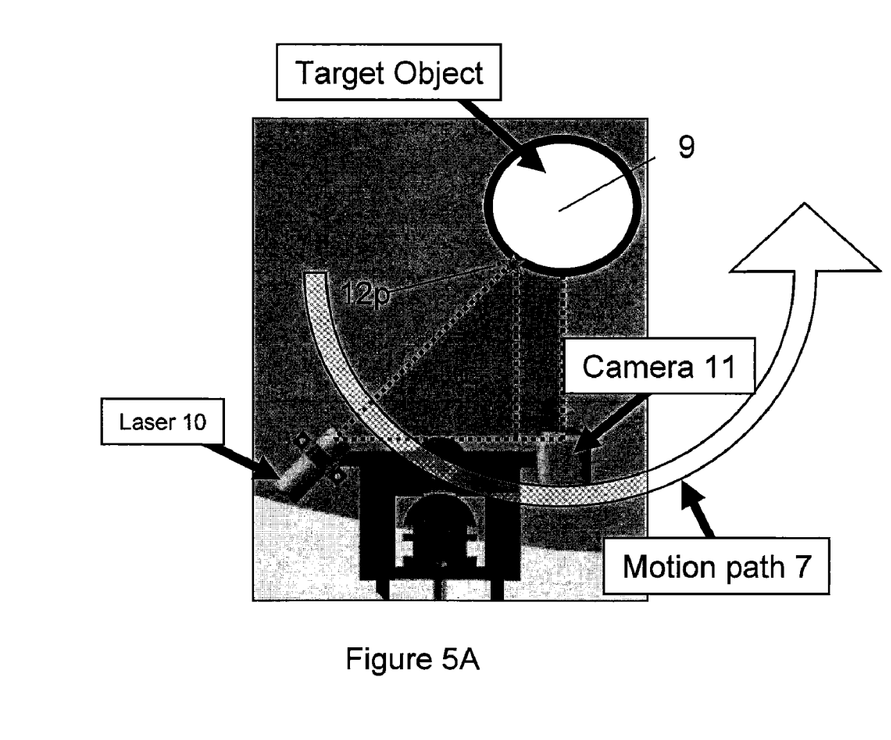
FIG. 5 illustrates the geometric relations between elements of the scan head and a location on a target object.
Figure 5B:
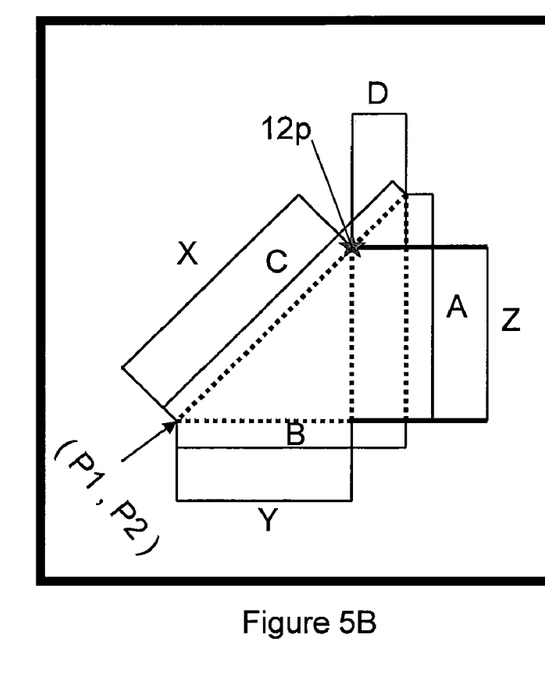
Figure 6A:
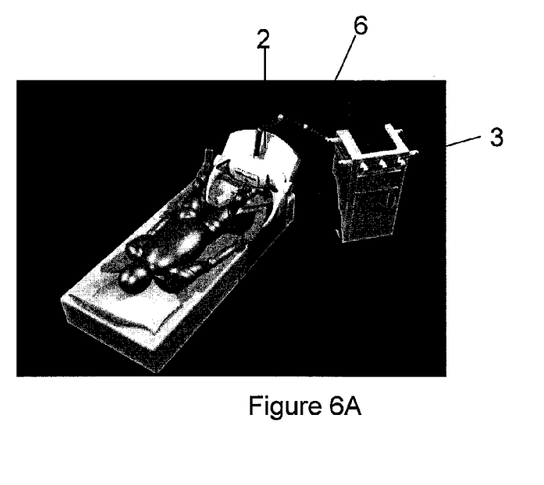
FIGS. 6A, 6B, 6C, and 6D illustrate exemplary clinical uses of an apparatus embodiment.
Figure 6B:
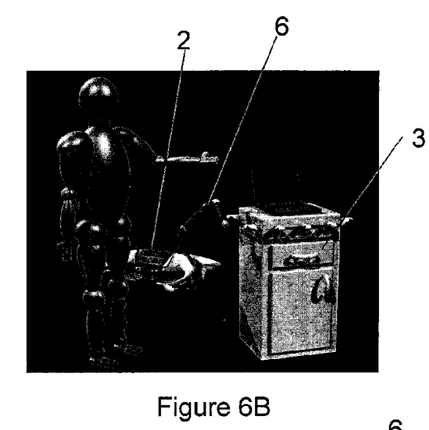
Figure 6C:
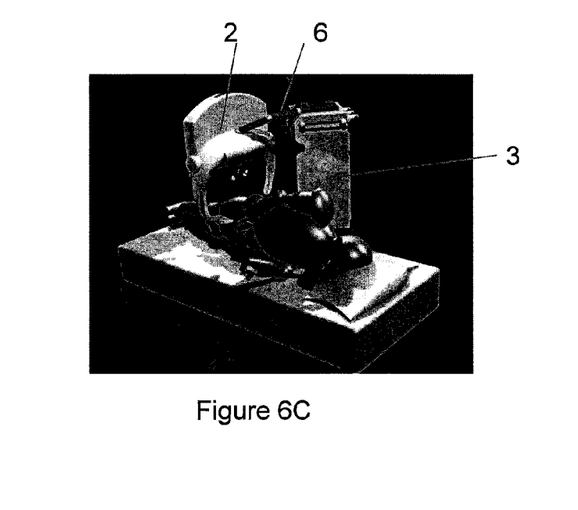
Figure 6D:
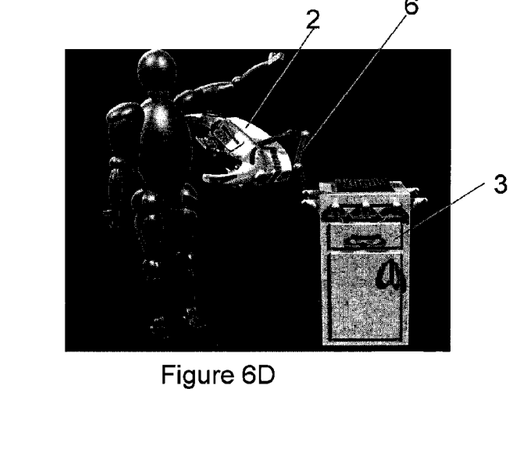

Referring now to FIG. 5A, a top view of scan head 4 in conjunction with a target object of inspection 9 is illustrated. FIG. 5B presents a simplified schematic diagram illustrating the geometric relationship of laser-line projector 10, image capturing device 11, and a point 12p on illumination line 12. Image capturing device 11 may capture an image of the projected contour line. The captured image is advantageously of digital form and includes a plurality of pixels. The captured image is stored in the processor for analysis. During operation, the scan head moves along the semi-circular path 7, while a series of images are captured by image capturing device 11.

The processor 3 is operable to control the apparatus as described above, and to analyze the resulting images. Because the projected illumination line has a known (calibrated) length, and the geometric relationship between the line-laser projector 10, and the image capturing device 11 is likewise known, analysis of the captured images using conventional triangulation methods can determine the coordinates in three axes of any pixel in the projected contour line. The processor 3 is operable to create a 3D model of a region of interest on the target object 9, e.g., a wound on a body part, from the three axis coordinates of a set of pixels, and determine the depth and perimeter of a wound or injury from the 3D model.

Referring to FIG. 6, examples of use of an embodiment of the present invention are provided. The apparatus is flexibly reconfigurable to permit diagnosis of an external wound of any size and located on virtually any part of a patient's anatomy whether the patient is lying down, sitting, or standing. A wound on the torso or on any extremity may be diagnosed using the apparatus.

Figure 7A:
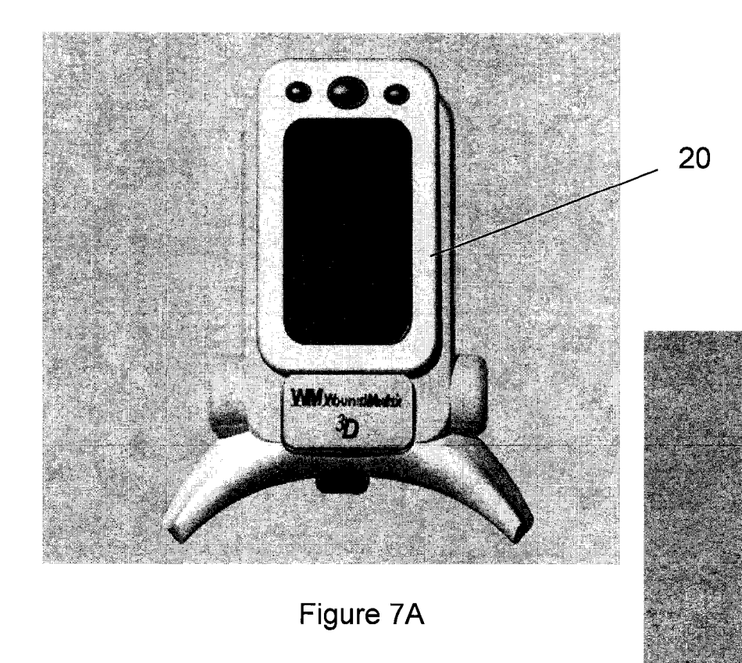
FIG. 7A illustrates a top view of a second embodiment of the configurable scanner.
Figure 7B:
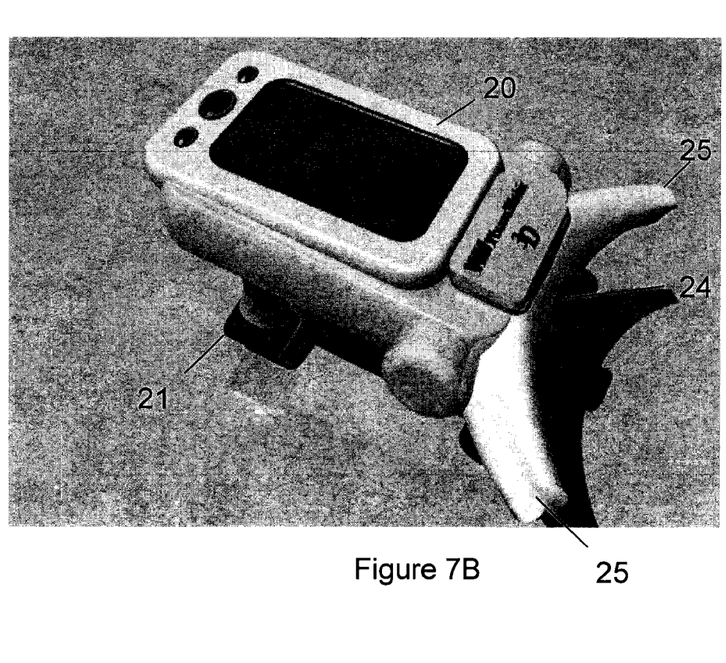
FIG. 7B illustrates a perspective view of the second embodiment of the configurable scanner.
Figure 8A:
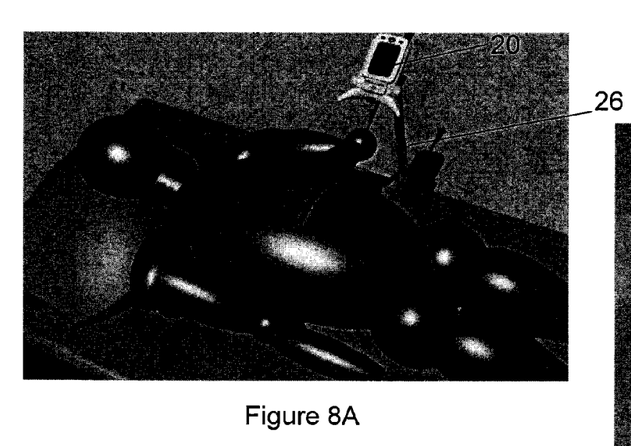
FIGS. 8A, 8B, and 8C illustrate exemplary clinical uses of the second embodiment of the configurable scanner
Figure 8B:
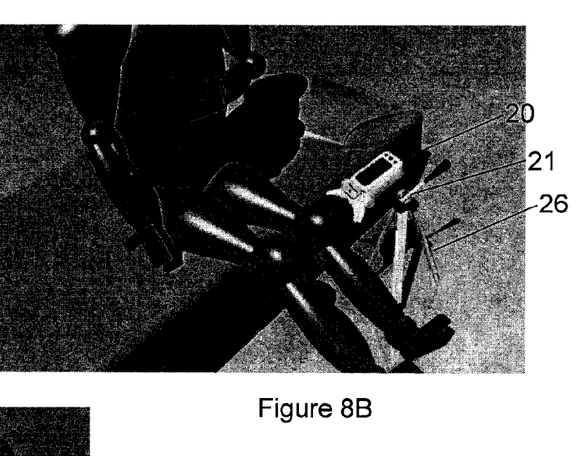
Figure 8C:
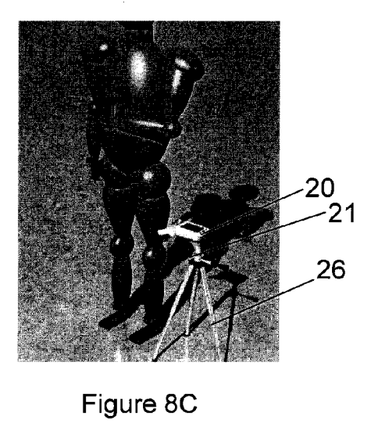

Referring now to FIG. 7, a second embodiment of the invention is depicted. Here, data capture device 20, includes scan head 24. Scan head 24 translates and rotates along an arc defined by arms 25 of the data capture device 20. Scan head 24 includes a line-laser projector and image capturing device (not shown). In an embodiment, however, the data capture device 20 stores imagery data for later processing and is not coupled during operation to a processor or work station. Conveniently, data capture device 20 includes a mounting interface 21 that permits mounting to a conventional tripod device 26, as shown, for example, in FIG. 8. Thus, in this embodiment, the invention results in a very compact diagnostic tool that can be advantageously used in a number of clinical settings.

Figure 9:
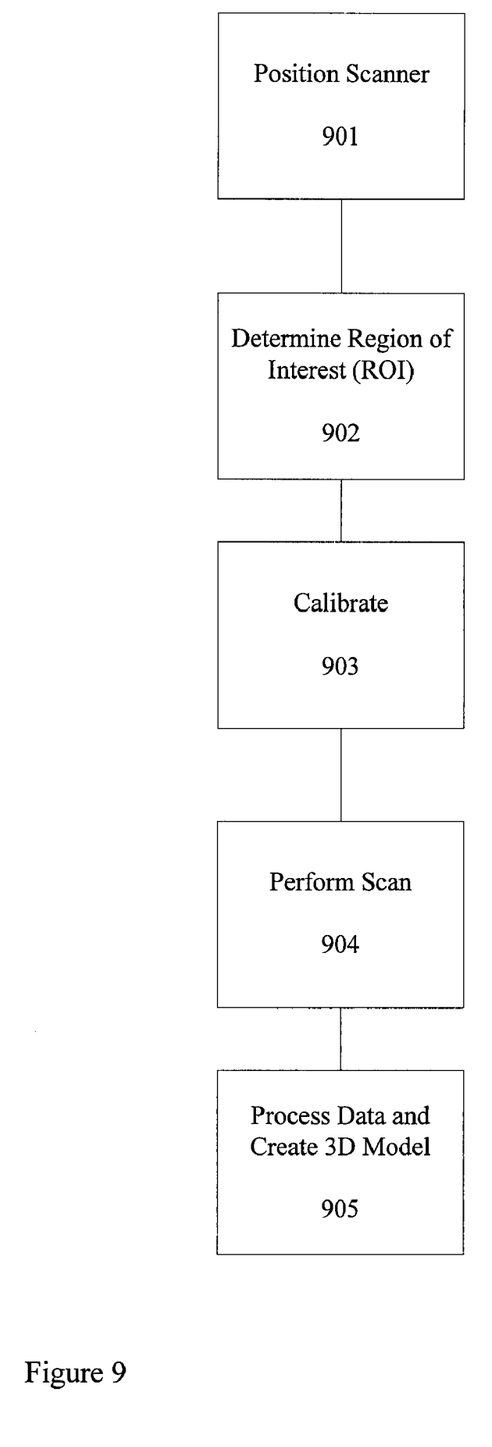
FIG. 9 illustrates a flow chart representative of a method embodiment.

A method embodiment of the invention will now be described with reference to FIG. 9:

Step 901: Position scanner

In a first step, the scanner is located so that the target object of inspection is proximate to the scanner center point. Typically, a user should place target object he/she wants to scan in front of the scanner, and use the guide lights/pointers to place the object into the scanner center point. The user may then utilize software to alert the scanner that the object is located at the scanner center point. The user or the software may then initiate step 902.

Step 902: Determine region of interest (ROI)

The scanner moves the scan head in a substantially semi circular motion, creating thereby a 180 degree view of the target area. This can be displayed in the view finder screen of a data capture device or at a user interface of a work station. The user may then be presented with the following options:

A. Run an edge detection procedure that highlights the wound areas;

B. Determine the wound area by drawing a rectangle around the area of interest; or C. Run a complete 180 degree scan.

Step 903: Calibrate

After the ROI has been determined, the scanner may start the calibration procedure by projecting laser line having a predefined length onto the surface of the target object. The scanner may use the predefined length laser line to adjust the device distance from the object by analyzing the images of the projected line. The scanner may command the motion arms to move and adjust the distance between the motion arms and the target object until the projected line reaches the desired number of pixels.

The scanner may perform the calibration procedure from more than one angle to determine the motion path. In an embodiment, the calibration procedure is performed from three angles.

Step 904: Perform scan

After the calibration is completed, the scanner may perform the actual scan, during which the scan head follows the motion path determined by the calibration step. During this process, the line-laser projector projects a laser line with a 45 degree angle (with respect to the optical axis of the image capture device) onto the target object surface. As the scan head translates around the substantially semicircular motion path, the image capture device takes images from a number of positions on the motion path. The images include the laser line as illuminated on the surface of the target object.

Step 905: Process data and create 3D Model

After the scan is completed, software may analyze and render the captured images, and save the data The foregoing merely illustrates principles of the invention. It will thus be appreciated that those skilled in the art will be able to devise numerous systems and methods which, although not explicitly shown or described herein, embody said principles of the invention and are thus within the spirit and scope of the invention as defined by the following claims.

What is claimed is:

1. Apparatus comprising:

a configurable scanner and a processor, the configurable scanner adapted for contactless measurement of volume of a wound on a target body part, said scanner comprising:

a scan head comprising a line-laser projector and an image capturing device; said projector operable to produce a contour line on the target body part and said image capturing device having a field of view inclusive of said contour line;

a scanning mechanism for translating the scan head along a motion path, said motion path being substantially semicircular and having a configurable radial distance from an imaginary axis;

a positioning mechanism for locating the scan head proximate to the target body part such that the imaginary axis is approximately coincident with an axis of the target body part; and means for calibrating the positioning mechanism and the scanning mechanism responsive to a feature of the target body part;

the processor operable to control a scanning procedure, said procedure comprising:

operating the scan head so as to project a contour line onto the surface of the target body part, said contour line having a calibrated length;

storing an image of the projected contour line captured by the image capturing device said image comprising a plurality of pixels; and moving the scan head a distance along the calibrated motion path and repeating said operating step;

and the processor further operable to analyze each captured image to determine the coordinates in three axes of at least one pixel of the projected contour line, said analyzing step comprising a calculation based on a known geometric relationship between the laser projector, the calibrated line length and the image capturing device;

create a 3D model of the region of interest; and determine a volume of the wound from the 3D model.

2. A method for contactless measurement of volume of a wound on a target body part, said method comprising:

positioning a configurable scanner, said scanner comprising a scan head, proximate to the target body part, said scanner further comprising a mechanism operable to translate the scan head along a motion path, said motion path being substantially semicircular and having a configurable radial distance from an imaginary axis, and said positioning step further comprising positioning said scanner such that the imaginary axis is approximately coincident with an axis of the target body part;

determining a region of interest on the target body, comprising at least the wound;

calibrating the configurable radial distance and the motion path;

operating the scan head, said scan head comprising a laser line projector and an image capturing device, said projector operable to produce a contour line on the target body part and said image capturing device having a field of view inclusive of said contour line, said operating step comprising:

projecting the contour line onto the surface of the target body part, said contour line having a calibrated length; and capturing an image of the projected contour line with the image capturing device said image comprising a plurality of pixels;

moving the scan head a distance along the calibrated motion path and repeating said operating step;

analyzing each captured image to determine the coordinates in three axes of at least one pixel of the projected contour line, said analyzing step comprising a calculation based on a known geometric relationship between the laser projector, the calibrated line length and the image capturing device;

creating a 3D model of the region of interest; and determining a volume of the wound from the 3D model.

* * * * *